(12) United States Patent
Wu et al.

(10) Patent No.: US 8,551,771 B2
(45) Date of Patent: Oct. 8, 2013

(54) APPARATUSES AND METHODS FOR GEL MOLDING AND CULTURE

(75) Inventors: Min-Hsien Wu, Kaohsiung (TW); Wan-Chen Tsai, Shengang Township (TW)

(73) Assignee: Chung Gung University, Tao-Yuan (TW)

( * ) Notice: Subject to any disclaimer, the term of this patent is extended or adjusted under 35 U.S.C. 154(b) by 775 days.

(21) Appl. No.: 12/653,335

(22) Filed: Dec. 10, 2009

(65) Prior Publication Data

US 2010/0273262 A1 Oct. 28, 2010

(30) Foreign Application Priority Data

Apr. 24, 2009 (TW) .............................. 98113647 A

(51) Int. Cl.
*C12M 1/36* (2006.01)
*C12M 1/38* (2006.01)
*C12M 3/00* (2006.01)
*C12M 1/12* (2006.01)
*C12M 1/22* (2006.01)

(52) U.S. Cl.
USPC .................. 435/305.2; 435/297.5; 435/305.1; 435/305.3; 435/305.4; 435/286.3

(58) Field of Classification Search
USPC ............................................ 435/283.1–309.4
See application file for complete search history.

(56) References Cited

U.S. PATENT DOCUMENTS

| | | | | |
|---|---|---|---|---|
| 4,349,632 | A | * | 9/1982 | Lyman et al. ............... 435/305.2 |
| 5,801,055 | A | * | 9/1998 | Henderson ................. 435/297.5 |
| 2008/0113573 | A1 | * | 5/2008 | Acosta et al. ................... 442/76 |

* cited by examiner

*Primary Examiner* — Nathan Bowers
*Assistant Examiner* — Lydia Edwards
(74) *Attorney, Agent, or Firm* — Kilpatrick Townsend & Stockton LLP

(57) ABSTRACT

A gel molding apparatus is adapted to be used in combination with a vessel that has a plurality of solution chambers, and includes a lid plate and a plurality of columns that project from a top surface of the lid plate. Each of the columns has a bottom side connected to the top surface of the lid plate, a top side opposite to the bottom side, and a well recessed from the top side for receiving a gel suspension and having a depth from the top side. A method for gel molding is conducted via the gel molding apparatus. A culture apparatus includes the vessel and the gel molding apparatus. A method for culture is performed through the culture apparatus.

4 Claims, 6 Drawing Sheets

APPARATUSES AND METHODS FOR GEL MOLDING AND CULTURE

CROSS-REFERENCE TO RELATED APPLICATION

This application claims priority to Taiwanese Application No. 098113647, filed Apr. 24, 2009, the disclosure of which is incorporated herein by reference.

BACKGROUND OF THE INVENTION

1. Field of the Invention

This invention relates to apparatuses and methods for gel molding and culture, more particularly to apparatuses and methods for high-throughput three-dimensional gel molding and culture.

2. Description of the Related Art

In research related to life science, culture (e.g., cell culture) is a basic laboratory technique. Cell culture mostly used in research is monolayer culture that belongs to 2-D (two-dimensional) culture. Cells show different physiology in 2-D and 3-D (three-dimensional) cell culture systems.

The 3-D cell culture system is able to establish environments that are more similar to in vivo environments, thereby inducing cell behavior that is more analogous to in vivo cell behavior. Consequently, 3-D cell culture is gradually regarded, and is widely adopted in studies related to drug screening and cell biology. In most processes of 3-D cell culture, gel is frequently utilized to entrap cells into a 3-D structure thereof. Therefore, preparation of the gel is required and includes quantification, dispensing, and molding of a gel suspension. However, conventional equipments and devices for liquid dispensing and quantification are not suitable for the gel suspension on account of viscous nature thereof. Thus, dispensing and quantification of the gel suspension may be inaccurate and may influence accuracy of experimental results.

Since high-throughput 3-D cell culture (e.g., 3-D cell culture using a commercial multi-well microplate) has been applied to numerous tasks (such as drug screening and toxin testing), a large amount of 3-D gel having small volume must be produced precisely and simultaneously. Accordingly, an apparatus and a method for efficiently achieving the aforementioned goal are in demand.

SUMMARY OF THE INVENTION

The object of the present invention is to provide apparatuses and methods for gel molding and culture in order to overcome the aforesaid drawbacks of the prior art.

According to one aspect of this invention, there is provided a gel molding apparatus that is adapted to be used in combination with a vessel having a plurality of solution chambers, and that includes a lid plate and a plurality of columns. Each of the columns projects from a top surface of the lid plate, and has a bottom side that is connected to the top surface of the lid plate, a top side that is opposite to the bottom side, and a well that is recessed from the top side for receiving a gel suspension and that has a depth from the top side. The depth of the well is relatively smaller than a height of a respective one of the columns from the top surface of the lid plate.

According to another aspect of this invention, there is provided a culture apparatus that includes a vessel and a gel molding apparatus. The vessel has a plurality of solution chambers. The gel molding apparatus includes a lid plate, and a plurality of columns that respectively have bottom sides connected to a top surface of the lid plate, top sides opposite to the bottom sides, and wells which are recessed from the top sides, respectively, for receiving a gel suspension. A depth of the wells from the topsides is relatively smaller than a height of the columns from the top surface of the lid plate. When the lid plate covers the vessel, the columns extend respectively into the solution chambers.

According to yet another aspect of this invention, there is provided a method for gel molding. The method comprises: providing a lid plate that has a plurality of columns, each of which has a well recessed from a top side thereof, and a perforated plate that has a plurality of through-holes; inserting the columns respectively into the through-holes so that the perforated plate is fitted to the lid plate; delivering a gel suspension onto the top sides of the columns and a top side of the perforated plate; and removing an excess amount of the gel suspension from the columns and the perforated plate such that the gel suspension is left in the wells.

According to still another aspect of this invention, there is provided a method for culture. The method comprises: providing a vessel that has a plurality of solution chambers, and a lid plate that has a plurality of columns having top sides respectively formed with wells; dispensing a gel suspension into the wells so that the gel suspension coagulates to form a plurality of gel modules; and inserting the columns into the solution chambers such that the lid plate covers the vessel and the gel modules contact a culture medium in the solution chambers.

BRIEF DESCRIPTION OF THE DRAWINGS

Other features and advantages of the present invention will become apparent in the following detailed description of the preferred embodiments of this invention, with reference to the accompanying drawings, in which.

DETAILED DESCRIPTION OF THE PREFERRED EMBODIMENTS

Figure 6A:
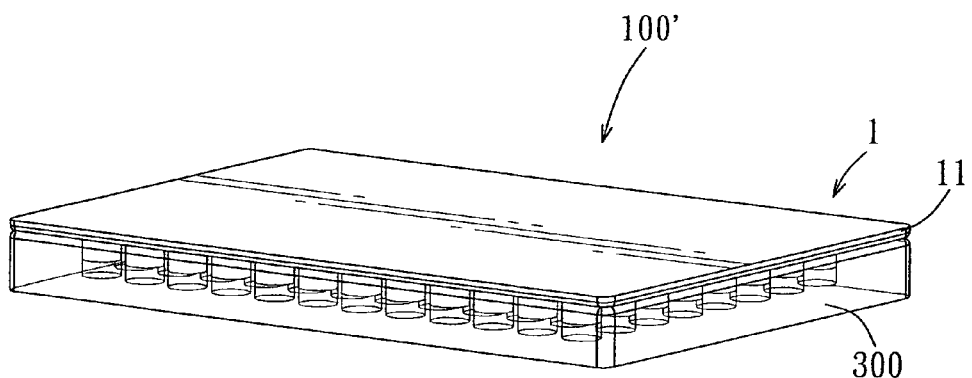
FIG. 6(a) is a perspective view of the preferred embodiment of a culture apparatus according to this invention.
Figure 6B:
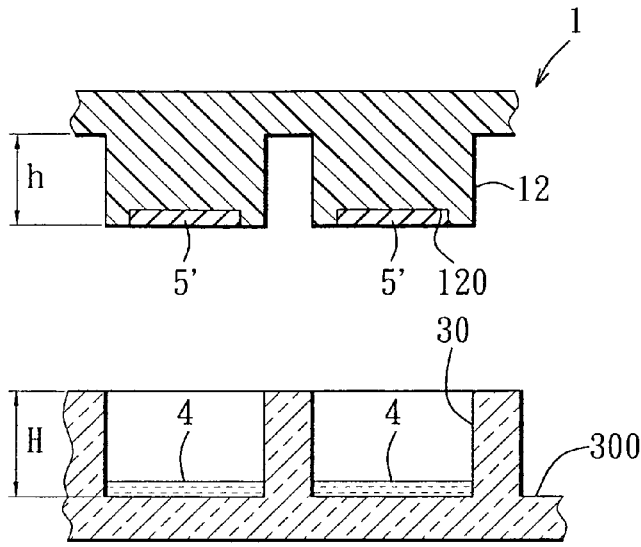
FIG. 6(b) is a fragmentary exploded sectional view to illustrate a mold that is separated from a vessel according to the preferred embodiment of the culture apparatus.
Figure 7:
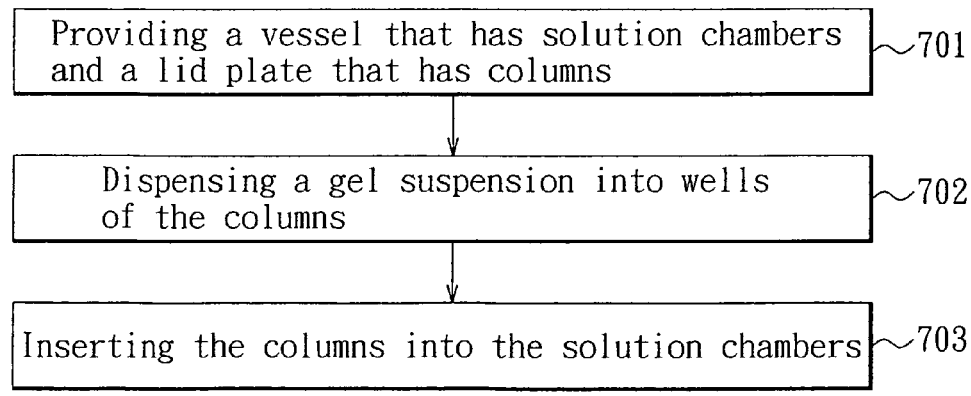
FIG. 7 is a flow chart of the preferred embodiment of a method for culture according to this invention.

Referring to FIGS. 1(a), 1(b), 2(a), and 2(b), the preferred embodiment of a gel molding apparatus 100 according to the present invention is adapted to be used in combination with a vessel 300 (see FIGS. 6(*a*) and 6(*b*)) that has a plurality of solution chambers 30 (see FIGS. 6(*a*) and 6(*b*)), and includes a mold 1.

The mold 1 has a lid plate 11 and a plurality of columns 12 that project from a top surface of the lid plate 11, and may be made of a soft or rigid polymeric material. In this embodiment, the mold 1 is designed as a multi-well microplate lid. The columns 12 are spaced apart from each other so that gaps 13 are formed among the columns 12. Each of the columns 12 has a bottom side 121 that is connected to the top surface of the lid plate 11, a top side 123 that is opposite to the bottom side 121, a surrounding wall 122 that interconnects the top and bottom sides 123, 121, and a well 120 that is recessed from the top side 123 for receiving a gel suspension and that has a depth from the top side 123. The depth of the well 120 is relatively smaller than a height (h) of a respective one of the columns 12 from the top surface of the lid plate 11. Precisely speaking, the height (h) of each of the columns 12 is equal to a distance between the top and bottom sides 123,121.

Specifications for the columns 12 can be customized according to the demand of end-users. For instance, a specification for the columns 12 can be customized so as to conform to a specification for wells of a culture device. Consequently, the height of the columns 12 is variable. For example, for a 96-well microplate (not shown), the height of the columns 12 may range from 5 mm to 10 mm so that top portions of the columns 12 can be immersed in a liquid (e.g., a liquid culture medium, a biochemical solution, or a reagent) inside the solution chambers 30 of the vessel 300 (see FIGS. 6(*a*) and 6(*b*)).

The wells 120 are adapted to mold and hold gel modules that have cells therein, and hence define the shapes and specification of the gel modules, such as the thicknesses and total volumes of the gel modules. The size of the wells 120 can be customized when needed. If the mold 1 is applied to the aforementioned 96-well microplate, the wells 120 may be provided with diameters ranging from 3 mm to 5 mm and depths ranging from 500 μm to 2 mm. When the gel molding apparatus 100 is commercialized, various specifications thereof can be provided in the market.

The gel molding apparatus 100 further includes a perforated plate 2 that is made of a rigid polymeric material. Referring back to FIGS. 2(*a*) and 2(*b*), the perforated plate 2 is fitted removably in the gaps 13 (see FIG. 1(*b*)) among the columns 12 and has a plurality of through-holes 20. Specifically, the columns 12 respectively extend through the through-holes 20 when the perforated plate 2 is fitted in the gaps 13 (see FIG. 1(*b*)) among the columns 12. Each of the through-holes 20 has a depth substantially equal to the height (h) of the columns 12 so that a top surface 21 of the perforated plate 2 is substantially flush with the surfaces of the top sides 123 of the columns 12. The resulting flush surfaces facilitate dispensing of a gel suspension into the wells 120.

Figure 1A:
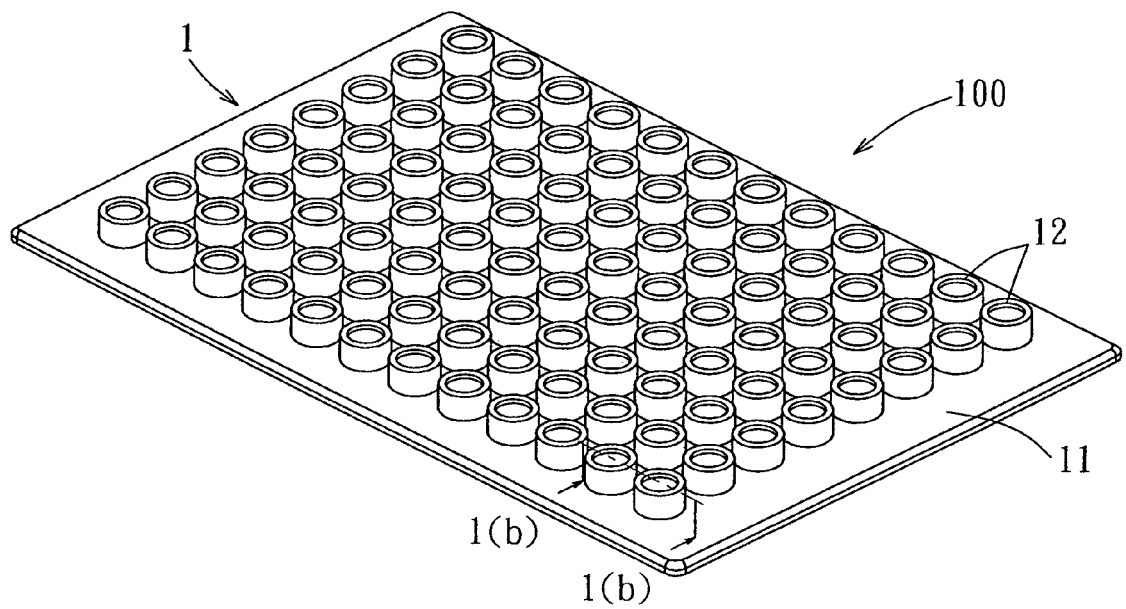
FIG. 1(a) is a perspective view of a mold of the preferred embodiment of a gel molding apparatus according to this invention.
Figure 1B:
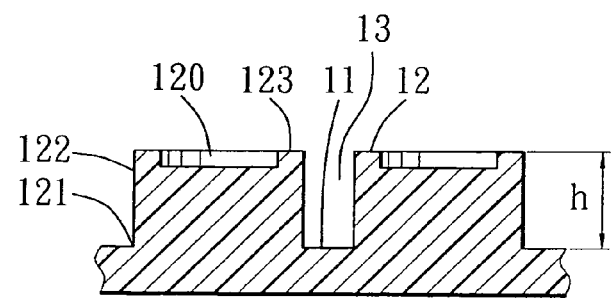
FIG. 1(b) is a fragmentary sectional view of the mold taken along line 1(b)-1(b) in FIG. 1(a)
Figure 2A:
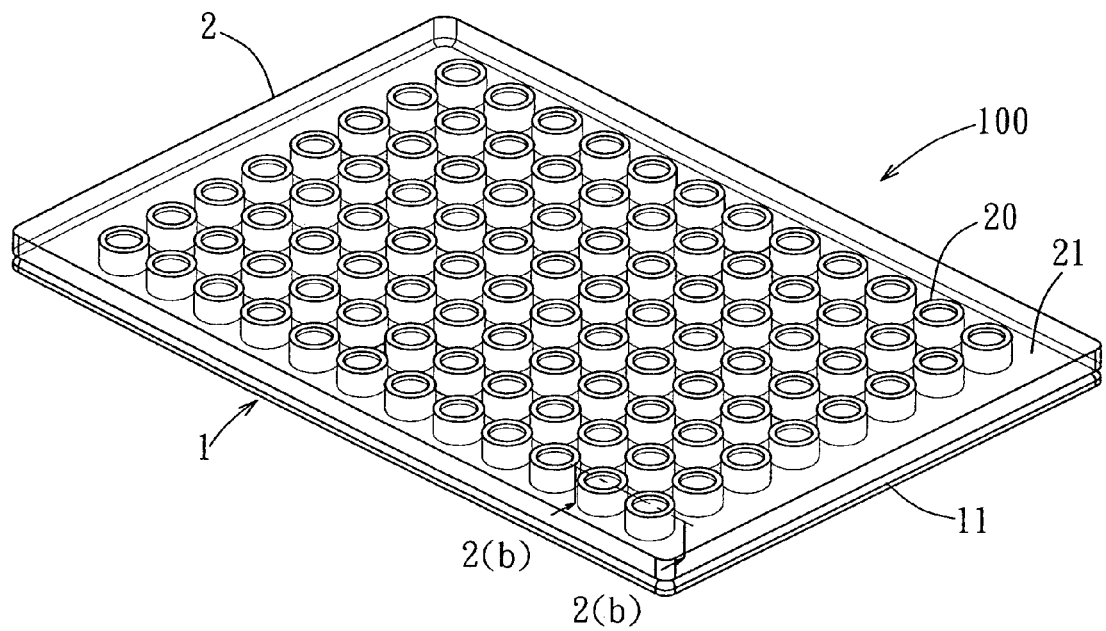
FIG. 2(a) is a perspective view of the preferred embodiment in an assembled state.
Figure 2B:
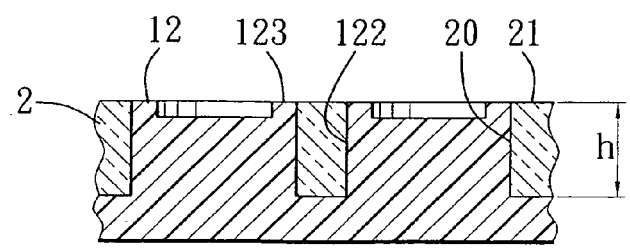
FIG. 2(b) is a fragmentary sectional view of the preferred embodiment taken along line 2(b)-2(b) in FIG. 2(a)
Figure 3A:
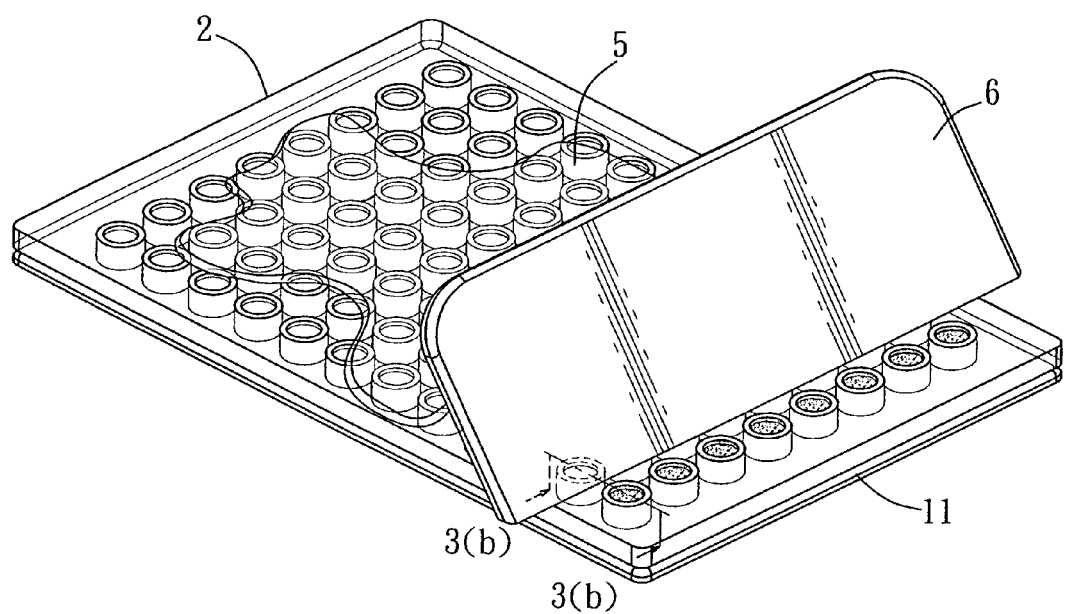
FIG. 3(a) is a perspective view illustrating how a gel suspension is dispensed into wells of columns of the mold using a scraper according to the preferred embodiment.
Figure 3B:
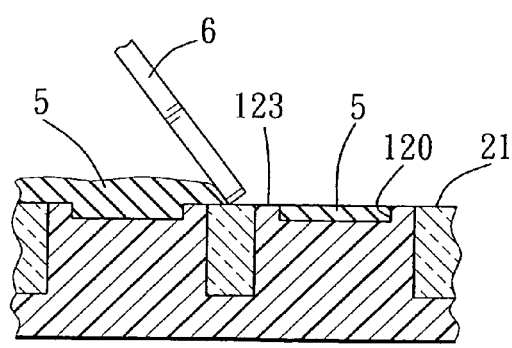
FIG. 3(b) is a fragmentary partly sectional view taken along line 3(b)-3(b) in FIG. 3(a)
Figure 4A:
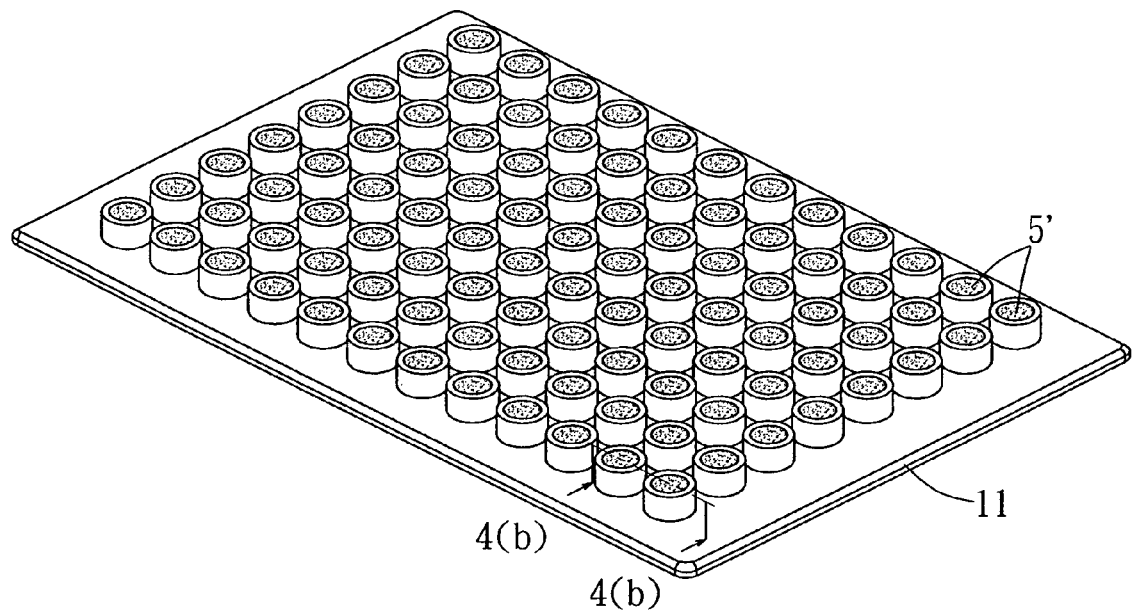
FIG. 4(a) is a perspective view to illustrate the mold that contains gel modules according to the preferred embodiment.
Figure 4B:
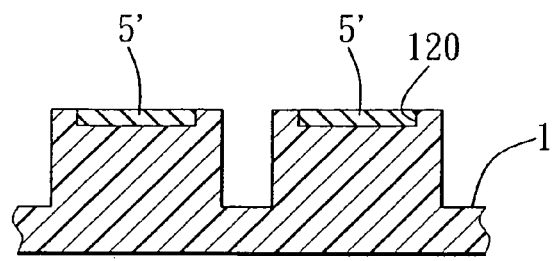
FIG. 4(b) is a fragmentary sectional view of the mold taken along line 4(b)-4(b) in FIG. 4(a)

According to the present invention, the preferred embodiment of a method for gel molding is described as follows. Referring to FIGS. 1(*a*), 1(*b*), and 5, in step 601, the mold 1 and the perforated plate 2 are provided. Referring to FIGS. 2(*a*), 2(*b*), and 5, in step 602, the columns 12 of the mold 1 are respectively inserted into the through-holes 20 of the perforated plate 2 so that the perforated plate 2 is fitted to the lid plate 11. Referring to FIGS. 3(*a*), 3(*b*), and 5, in step 603, a gel suspension 5 is delivered onto the top sides 123 of the columns 12 and the top surface 21 of the perforated plate 2, and a scraper 6 is used for dispensing the gel suspension 5 into each of the wells 120. An excess amount of the gel suspension 5 is removed from the top sides 123 of the columns 12 and the top surface 21 of the perforated plate 2 by dint of the scraper 6 such that the gel suspension 5 is left in the wells 120. The gel suspension 5 contains desired biological samples such as cells, tissues, or microbes, or chemicals such as drugs. The gel suspension 5 may be made of a gel material for 3-D cell culture. Examples of the gel material include natural and synthetic hydrogel. Referring to FIGS. 4(*a*), 4(*b*), and 5, in step 604, when the gel suspension 5 (see FIGS. 3(*a*) and 3(*b*)) coagulates to form a plurality of gel modules 5', the perforated plate 2 (see FIGS. 3(*a*) and 3(*b*)) is removed from the mold 1. Thus, the method for gel molding is completed, and is able to efficiently and simultaneously produce a large number of the gel modules 5' that have the same specifications. The gel modules 5' are suitable for 3-D cell culture, immobilization of cells and biological molecules, drug testing and screening, toxin testing, enzyme immobilization, and the study of drug delivery.

Referring to FIGS. 6(*a*) and 6(*b*), the preferred embodiment of a culture apparatus 100' according to the present invention includes the mold 1 and the vessel 300 that has a plurality of the solution chambers 30. When the lid plate 11 of the mold 1 covers the vessel 300, the columns 12 of the mold 1 extend respectively into the solution chambers 30. It should be noted that the culture apparatus 100' could further include the perforated plate 2 (see FIGS. 2(*a*) and 2(*b*)) in other embodiments.

In this embodiment, the vessel 300 is a multi-well microplate. Each of the solution chambers 30 has a depth (H) that is greater than the height (h) of each of the columns 12.

Figure 5:
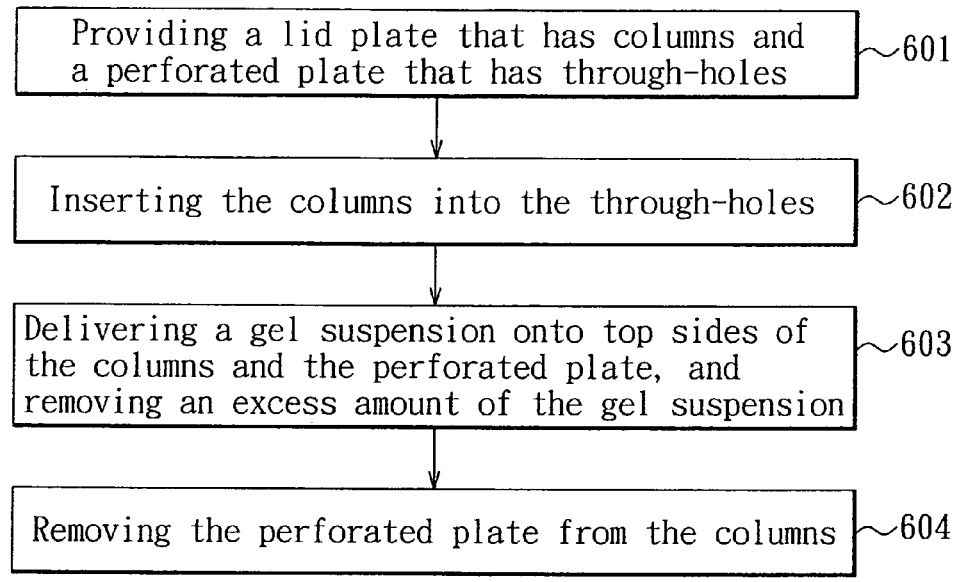
FIG. 5 is a flow chart of the preferred embodiment of a method for gel molding according to this invention.

According to the present invention, the preferred embodiment of a method for culture is described below. Referring to FIGS. 6(*a*) and 7, in step 701, the vessel 300 and the mold 1 are provided. A culture medium 4 (shown in FIG. 6(*b*)) is disposed in the solution chambers 30 before the method is conducted. Referring to FIGS. 3(*a*), 3(*b*), 4(*a*), 4(*b*), and 7, in step 702, the gel suspension 5 is delivered into the wells 120 so that the gel suspension 5 coagulates to form a plurality of the gel modules 5'. The formation of the gel modules 5' is performed through steps 601-604 (shown in FIG. 5) of the method for gel molding. By virtue of the perforated plate 2 and the scraper 6, the gel suspension 5 can be dispensed into the wells 120. Referring to FIGS. 6(*a*), 6(*b*), and 7, in step 703, the columns 12 are inserted into the solution chambers 30 such that the lid plate 11 covers the vessel 300 and the gel modules 5' contact the culture medium 4 in the solution chambers 30. Since the gel modules 5' can be immersed in the culture medium 4, the biological samples in the gel modules 5' are able to obtain nutrients in the culture medium 4.

Some advantages with regard to the gel molding apparatus 100, the culture apparatus 100', and the methods for gel molding and culture are as follows:

1. The mold 1 is compatible with a suitable commercial laboratory culture vessel (e.g., a multi-well microplate, a bioreactor, etc.), and can serve as a lid to cover the culture vessel, thereby providing a sterile environment for cell culture. In addition, the mold 1 has a simple structure such that a production cost thereof is low, can be easily operated, and is an efficient high-throughput 3-D culture device.

2. The 3-D gel modules 5' in the wells 120 of the mold 1 can be easily and rapidly separated from the culture medium 4 in the solution chambers 30 of the vessel 300.

3. The gel modules 5' can be stained with reagent for further high-throughput analysis employing an optical screening device, such as a microplate reader.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A gel molding apparatus adapted to be used in combination with a vessel that has a plurality of solution chambers, said gel molding apparatus comprising:
a lid plate;
a plurality of columns that project from a top surface of said lid plate, each of said columns having a bottom side that is connected to said top surface of said lid plate, a top side that is opposite to said bottom side, and a well that is recessed from said top side for receiving a gel suspension; and
a perforated plate having a plurality of through-holes, said columns respectively extending through said through-holes such that said perforated plate fills gaps formed among said columns, each of said through-holes having a depth substantially equal to said heights of said columns so that a top surface of said perforated plate is substantially flush with said top sides of said columns.

2. A culture apparatus comprising:
a vessel having a plurality of solution chambers; and
a gel molding apparatus including a lid plate, and a plurality of columns that respectively have bottom sides connected to a top surface of said lid plate, top sides opposite to said bottom sides, and wells which are recessed from said top sides, respectively, for receiving a gel suspension, a depth of said wells from said top sides being relatively smaller than a height of said columns from said top surface of said lid plate;
wherein, when said lid plate covers said vessel, said columns extend respectively into said solution chambers, and said lid plate completely covers all of said solution chambers as a lid, and wherein said lid plate has no opening for access to said solution chamber.

3. The culture apparatus as claimed in claim 2, wherein said gel molding apparatus further includes a perforated plate having a plurality of through-holes, wherein, when said perforated plate is disposed over said lid plate, said columns respectively extend through said through-holes, a top surface of said perforated plate is substantially flush with said top sides of said columns.

4. A method for gel molding comprising:
providing a lid plate that has a plurality of columns projecting therefrom, and a perforated plate that has a plurality of through-holes, each of the columns having a well recessed from a top side thereof;
disposing the perforated plate over the lid plate and inserting the columns respectively into the through-holes such that the perforated plate fills gaps formed among the columns and such that a top side of the perforated plate is substantially flush with the top sides of the columns;
delivering a gel suspension onto the top sides of the columns and the top side of the perforated plate; and
removing an excess amount of the gel suspension from the columns and the perforated plate using a scraper such that the gel suspension is left in the wells.

* * * * *